United States Patent
Jang et al.

(10) Patent No.: US 8,372,811 B2
(45) Date of Patent: Feb. 12, 2013

(54) COMPOSITION FOR TREATING RETINOPATHY OR GLAUCOMA COMPRISING THROMBIN DERIVED PEPTIDES

(75) Inventors: Jin Wook Jang, Seoul (KR); Hyeong Joon Lim, Goyang-si (KR); Yang Je Cho, Seoul (KR); Won Il Yoo, Seoul (KR); Doo Sik Kim, Seoul (KR); Oh Woong Kwon, Seoul (KR); Kyoung Chul Ko, Seoul (KR); Kyung Sul Kim, Seoul (KR)

(73) Assignee: Eyegene, Inc., Seoul (KR)

( * ) Notice: Subject to any disclaimer, the term of this patent is extended or adjusted under 35 U.S.C. 154(b) by 367 days.

(21) Appl. No.: 12/678,898

(22) PCT Filed: Sep. 21, 2007

(86) PCT No.: PCT/KR2007/004636
§ 371 (c)(1),
(2), (4) Date: Apr. 5, 2010

(87) PCT Pub. No.: WO2009/038243
PCT Pub. Date: Mar. 26, 2009

(65) Prior Publication Data
US 2010/0297100 A1    Nov. 25, 2010

(51) Int. Cl.
*C07K 14/515*    (2006.01)
*A61K 38/00*    (2006.01)

(52) U.S. Cl. ........ 514/13.3; 514/1.1; 514/14.7; 530/300

(58) Field of Classification Search ........................ None
See application file for complete search history.

(56) References Cited

U.S. PATENT DOCUMENTS 5,674,888 A * 10/1997 Polansky et al. .............. 514/418
2003/0125351 A1 * 7/2003 Azuma et al. ................. 514/300
2007/0282095 A1    12/2007 Hosokawa et al.

FOREIGN PATENT DOCUMENTS

WO    WO 2005/089070 A2    9/2005

OTHER PUBLICATIONS

Lee et al. (1998) Angle-Closure Glaucoma After Laser Treatment for Retinopathy of Prematurity, J. AAPOS, vol. 2, pp. 383-384.*
Canadian Bio Med System (2012, updated),www.canadianbiomed.com/news.html, pp. 1-4.*
Iris melanoma (2012, updated) http://www.eyecancer.com/patient/Condition.aspx?nID=28&Category=Iris+Tumors&Condition=Iris+Melanoma, pp. 1-2.*
Dardik et al., "Factor XIII (FXIII) and Angiogenesis," J. Thromb, Haemost 4:19-25, 2006.
Wang et al., "Thrombin Peptide (TP508) Promotes Fracture Repair by Up-Regulating Inflammatory Mediators, Early Growth Factors, and Increasing Angiogenesis," J. Orthop, Res. 23:671-679, 2005.
International Search Report from International Application No. PCT/KR2007/004636, dated Apr. 8, 2008 (date of completion of search) and Apr. 10, 2008 (date of mailing of report).

* cited by examiner

*Primary Examiner* — Manjunath Rao
*Assistant Examiner* — Samuel Liu
(74) *Attorney, Agent, or Firm* — Clark & Elbing LLP

(57) ABSTRACT

Disclosed is a composition for treating retinopathy comprising thrombin derived peptide as an effective component.

4 Claims, 4 Drawing Sheets

(B)

(A)

(B)

(A)

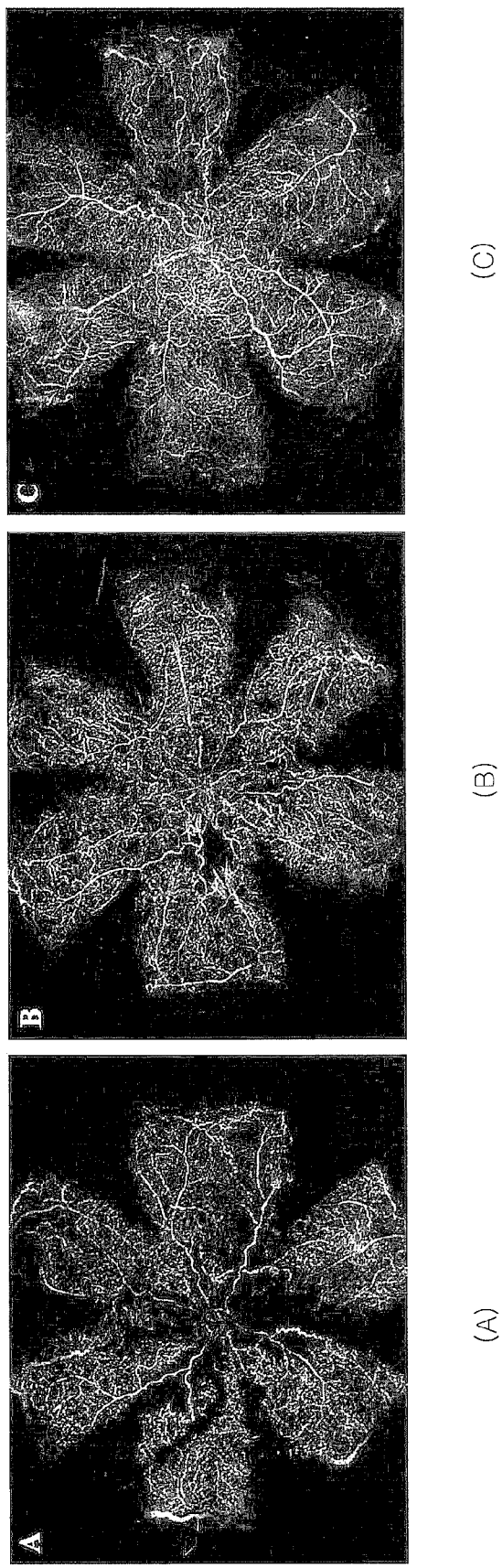

SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Cyclo(-Arg-Gly-Asp-D-Phe-Val) derived from Homo
      sapiens

<400> SEQUENCE: 1

Arg Gly Asp Phe Val
1               5

<210> SEQ ID NO 2
<211> LENGTH: 10
<212> TYPE: PRT
<213> ORGANISM: Artificial Sequence
<220> FEATURE:
<223> OTHER INFORMATION: H-Gly-Phe-Gly-Arg-Gly-Asp-Ser-Pro-Cys-Ala-OH
      derived from Homo sapiens

<400> SEQUENCE: 2

Gly Phe Gly Arg Gly Asp Ser Pro Cys Ala
1               5                   10

<210> SEQ ID NO 3
<211> LENGTH: 25
<212> TYPE: PRT
<213> ORGANISM: Artificial Sequence
<220> FEATURE:
<223> OTHER INFORMATION: peptide derived from Homo sapiens

<400> SEQUENCE: 3

Ala Gly Tyr Lys Pro Asp Glu Gly Lys Arg Gly Asp Gly Asp Ala Cys
1               5                   10                  15
Glu Gly Asp Ser Gly Gly Pro Phe Val
            20                  25

<210> SEQ ID NO 4
<211> LENGTH: 624
<212> TYPE: PRT
<213> ORGANISM: Artificial Sequence -continued
<220> FEATURE:
<223> OTHER INFORMATION: thrombin-like peptide derived from Homo sapiens

<400> SEQUENCE: 4

```
Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Ser Arg Glu Gly Ser Ser Val Asn Leu Ser Pro
        195                 200                 205

Pro Leu Glu Gln Cys Val Pro Asp Arg Gly Gln Gln Tyr Gln Gly Arg
210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Gln Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Glu Thr Gly Asp Gly Leu Asp
290                 295                 300

Glu Asp Ser Asp Arg Ala Ile Glu Gly Arg Thr Ala Thr Ser Glu Gly
305                 310                 315                 320

Gly Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Ile Phe Gly Met
370                 375                 380

Ser Pro Trp Gln Val Met Cys Gly Ala Ser Leu Ile Ser Asp Arg Trp
385                 390                 395                 400
```

-continued

Val Leu Thr Ala Ala His Cys Leu Leu Tyr Pro Pro Trp Asp Lys Asn
            405                 410                 415

Phe Thr Glu Asn Asp Leu Leu Val Arg Ile Gly Lys His Ser Arg Thr
            420                 425                 430

Arg Tyr Glu Arg Asn Ile Glu Ser Ile Ser Met Leu Glu Lys Ile Tyr
            435                 440                 445

Ile His Pro Arg Tyr Asn Trp Arg Glu Asn Leu Asp Arg Asp Ile Ala
            450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
            485                 490                 495

Tyr Lys Gly Arg Val Thr Ala Asn Val Gly Lys Gly Gln Pro Trp Thr
            500                 505                 510

Ala Asn Val Gly Lys Gly Gln Pro Ser Val Leu Gln Val Val Asn Leu
            515                 520                 525

Pro Ile Val Glu Arg Pro Val Cys Lys Asp Ser Thr Arg Ile Arg Ile
            530                 535                 540

Thr Asp Asn Met Phe Cys Ala Gly Tyr Lys Pro Asp Glu Gly Lys Arg
545                 550                 555                 560

Gly Asp Gly Asp Ala Cys Glu Gly Asp Ser Gly Gly Pro Phe Val Met
            565                 570                 575

Lys Ser Pro Phe Asn Asn Arg Trp Tyr Gln Met Gly Ile Val Ser Trp
            580                 585                 590

Gly Glu Gly Cys Asp Arg Asp Gly Lys Tyr Gly Phe Tyr Thr His Val
            595                 600                 605

Phe Arg Leu Lys Lys Trp Ile Gln Lys Val Ile Asp Gln Phe Gly Glu
            610                 615                 620

<210> SEQ ID NO 5
<211> LENGTH: 42
<212> TYPE: PRT
<213> ORGANISM: Artificial Sequence
<220> FEATURE:
<223> OTHER INFORMATION: thrombin derivative peptide derived from Homo
      sapiens

<400> SEQUENCE: 5

Arg Ile Arg Ile Thr Asp Asn Met Phe Cys Ala Gly Tyr Lys Pro Asp
1               5                   10                  15

Glu Gly Lys Arg Gly Asp Gly Asp Ala Cys Glu Gly Asp Ser Gly Gly
            20                  25                  30

Pro Phe Val Met Lys Ser Pro Phe Asn Asn
            35                  40

<210> SEQ ID NO 6
<211> LENGTH: 15
<212> TYPE: PRT
<213> ORGANISM: Artificial Sequence
<220> FEATURE:
<223> OTHER INFORMATION: thrombin derivative peptide derived from Homo
      sapiens

<400> SEQUENCE: 6

Asp Glu Gly Lys Arg Gly Asp Gly Asp Ala Cys Glu Gly Asp Ser
1               5                   10                  15

COMPOSITION FOR TREATING RETINOPATHY OR GLAUCOMA COMPRISING THROMBIN DERIVED PEPTIDES

CROSS-REFERENCE TO RELATED APPLICATIONS

This application is the U.S. national stage filing under 35 U.S.C. §371 of international application PCT/KR2007/004636, filed Sep. 21, 2007.

TECHNICAL FIELD

The present invention relates to a composition for treating ophthalmology disease comprising thrombin derived peptide.

BACKGROUND ART

Generally, representative ophthalmology diseases in reference to angiogenesis are Diabetic retinopathy and Retinopathy of prematurity which blood vessels are formed in the cornea, and Age-related macular degeneration which blood vessels are formed in the choroid (Amal A. E. et al., Retina 11:244-249(1991); Constantin J. P. et al., Ophthalmology 97:1329-1333(1990); Jin-Hong C. et al., Current opinion in Ophthalmology 12:242-249(2001);Peter A. C., J of Cellular Physiology 184:301-310(2000)) and Glaucoma.

Retinopathy of prematurity (ROP) is a major cause of loss of eyesight in infants and occurs through two-step. Premature infants have an incomplete retinal blood vessel at the beginning of a birth, especially the premature infants who suffer from the progress of ROP have a risk of inducing no growth of blood vessel in a retina (Flynn J. T. et al., Arch Ophthalmol 95:217-223 (1977)). As a result, the retina is formed in a blood vessel-free state, resulting in formation of a low-oxygen peripheral retina (step 1 of ROP). In such step 1 of ROP, a non-perfusion level of retina determines a destructive stage including a retinal detachment and blindness caused by angiogenesis (step 2 of ROP) (Penn J. S. et al., Invest Ophthalmol Vis Sci 35:3429-435 (1994)). If blood vessel is normally developed in the retina of the premature infants, then a destructive stage may not be initiated due to a secondary angiogenesis in ROP. It has been known that use of high concentration of oxygen is associated with such diseases, which means that an oxygen-regulated factor is present in the retina of premature infants.

It is anticipated that vascular endothelial growth factor (VEGF), which is necessarily required to a normal angiogenesis and known as a oxygen-regulated factor, should take a important role in ROP, but it is known from the various studies that VEGF act mainly in the first and secondary stage of ROP (Pierce E.A. et al., Arch Ophthalmol 114:1219-1228 (1996)). It was studied that VEGF expression is inhibited in the first stage to affect the growth of blood vessel, using ROP animal model (for example, high supplement oxygen).

Diabetic retinopathy is one of the most well known conditions among microvessel-related complication mainly caused by hyperglycemia, and become a primary cause of acquired loss of sight in the adult (Brownlee M., Nature 414:813-820 (2001)). A serious loss of sight associated with diabetic retinopathy is generated by means to retinal angiogenesis (Battegay E. J., J Mol Med 73:333-346 (1995)) and therefore vitreous hemorrhage and 4 tractional retinal detachment (Cai J., Boulton M., Eye 16:242-260(2002)). Referring to a pathophysiological change in the retina of diabetic patients, the conditions such as loss of cells surrounding capillary vessel, growth of basement membrane, loss of automatic control function in retinal blood vessel, abnormality of capillary circulation, microaneurysm, IRMA (intraretinal microvascular abnormalities) have appeared, finally resulting in formation of an area of retinal non-perfusion (Lip P. L. et al., Invest Ophthalmol Vis Sci 41:2115-2119 (2000); Hammes H. P. et al., Diabetes 51:3107-3112 (2002)). Such changes induce an increased vascular permeability, chronic retinal hypoxia and retinal ischemia through their continuous development to form macular edema or angiogenesis, resulting in progress into proliferative diabetic retinopathy (Aiello L. P. et al., Diabetes Care 21:143-156 (1998)). It seems that diabetic patients have an increased level of a factor VEGF, and then the increased factor induces a retinopathy by destroying a retinal blood barrier.

Age-related macular degeneration is one of the major causes of blindness which appears over 50 years old. Severe loss of sight results from angiogenesis induced from capillary vessel of a choroidal neovascular membrane (Ferris F. L. 3rd et al., Arch Ophthalmol 102:1640-1642 (1984)). AMD is generally divided in 2 different types, for example wet AMD and dry AMD. It was known that development of wet AMD was followed by dry AMD. Dry AMD is referred to as the presence of macular degeneration due to pigmentary degeneration of retina and loss of retinal pigment epithelium (RPE). As the modified form of dry AMD, wet AMD shows conditions of subretinal neovascularization (subretinal scar), subretinal hemorrhage, detachment of RPE. In fact, subretinal neovascularization is meant to be a growing cicatricial tissue for a treatment of a space resulting from diseased RPE. Growth of neovascularization allows plasma and cellulose to be extruded therefrom, causing a small retinal detachment (Mousa S. A. et al., J Cell Biochem 74:135-43 (1999)). In addition, an injury caused by cicatrix of subretinal membrane may also result in weak eyesight.

Now, the method used to treat such ocular diseases includes laser treatment, laser photocoagulation, cryocoagulation and Visudyne (Edwin E. B. et al., Ophthalmology 88:101-107 (1981)). All of such treatments are carried out by surgery, but treatment by therapeutic agents still remains to be developed. Treatment by surgery has significant problems of incapable to be applied to all patients, and it also has disadvantages of having low healing possibilities and very expensive cost. Accordingly, most of patients, who may not receive a surgery, may come to blindness due to the lack of specific therapeutic agents. Also as human lives longer, these conditions continue to increase, but the therapeutic agents still remain to be developed. Thus, many studies and developments of angiogenesis inhibitors and therapeutic agents for treating the ocular diseases are still carried out. And examples of such agents include steroids, MMP inhibitor, antibodies against angiogenic growth factor and so on (Jeremy G. et al., Am J Pathology 160:1097-1103(2002)).

DISCLOSURE OF INVENTION

Accordingly, the present invention is designed to solve the problems of the prior art, and therefore it is an object of the present invention to provide a composition for treating ophthalmology disease.

In order to accomplish the above object, the present invention provides a composition for treating retinopathy or glaucoma comprising a thrombin derived peptide as an effective component.

The term "thrombin derived peptide" is used herein to mean a peptide, e.g., about 15 to 50 residues of amino acids including the peptide set forth in SEQ ID NO: 6 as a core sequence and the full sequence of thrombin also can be included in the scope of the peptide.

In the preferred embodiment of the present invention, thrombin derived peptide is the peptide set forth in SEQ ID NO: 6 or is preferably some amino acids are added to N-terminal or C-terminal of the peptide set forth in SEQ ID NO: 6(i.e., the peptide sequence set forth in SEQ ID NO: 3, SEQ ID NO: 5 or SEQ ID NO: 4) but is not particularly limited to the peptides.

In the preferred embodiment of the present invention, the ophthalmology disease includes disease, but are not particularly limited to, selected from the group consisting of diabetic retinopathy, retinopathy of prematurity, age-related macular degeneration, and glaucoma.

The peptides of the present invention reduce the abnormal formation of the vessels generated in retinopathy and stimulate the normal formation of vessels and decrease the leakage of the blood.

The formulation for treating eye diseases includes for example eye drop, eye ointment, oral preparation or percutaneously absorbable preparation.

The formulation used for administration of the compound into the subTenon's space of the eye can be any form suitable for application into the subTenon's space by injection through a cannula with small diameter suitable for injection into the subTenon's space. Examples for injectable application forms are solutions, suspensions or colloidal suspensions.

Compositions usable for injection into the subTenon's space contain a physiologically tolerable carrier together with the relevant agent as described herein, dissolved or dispersed therein as an active ingredient.

As used herein, the term"pharmaceutically acceptable" refers to compositions, carriers, diluents and reagents which represent materials that are capable of administration into the subTenon's space of a mammal without the production of undesirable physiological effects. The preparation of an injectable pharmacological composition that contains active ingredients dissolved or dispersed therein is well understood in the art and need not be limited based on formulation. The preparation can also be emulsified. The active ingredient can be mixed with excipients which are pharmaceutically acceptable and compatible with the active ingredient and in amounts suitable for use in the therapeutic methods described herein.

Suitable excipients are, for example, water, saline, sorbitol, glycerol or the like and combinations thereof. In addition, if desired, the composition can contain minor amounts of auxiliary substances such as wetting or emulsifying agents, pH buffering agents, and the like which enhance the effectiveness of the active ingredient. The composition can also contain viscosity enhancing agents like hyaluronic acid.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, sorbitol and other solutes.

Depending from the application form the active compound liberates in an immediate or a sustained release manner. A sustained release formulation is preferred because the injection frequency can be reduced.

One possibility to achieve sustained release kinetics is embedding or encapsulating the active compound into nanoparticles. Nanoparticles can be administrated as powder, as powder mixture with added excipients or as suspensions. Colloidal suspensions of nanoparticles are preferred because they can easily be administrated through a cannula with small diameter.

Liposomes are a further drug delivery system which is easily injectable. Accordingly, in the method of invention the active compounds can also be administered into the subTenon's space of the eye in the form of a liposome delivery system. Liposomes are well-known by a person skilled in the art.

Liposomes can be formed from a variety of phospholipids, such as cholesterol, stearylamine of phosphatidylcholines. Liposomes being usable for the method of invention encompass all types of liposomes including, but not limited to, small unilamellar vesicles, large unilamellar vesicles and multilamellar vesicles.

The term "the pharmaceutically effective amount", "pharmaceutical effective amount" or "effective component" is used herein to mean the amount of drug or medicine which induces biological response or medicinal response of tissue, system animal or human which researchers or doctors are desired. Proper response includes the prevention of onset of the disease, the prevention of progress of the disease or the regression of the disease.

In the preferred embodiment, the administration of pharmaceutically effective amount of the present invention treats retinopathy, more preferably diabetic retinopathy, retinopathy of prematurity, and age-related macular degeneration.

The term "treating retinopathy" is used herein to include decreasing the abnormal angiogenesis, inducing the normal angiogenesis, decreasing the vascular leakage, and assisting stabilization of the blood vessels but is not limited to the description.

The pharmaceutical composition of the present invention may be administered tropically or systemically. The systemic application includes oral, transdermal, subcutaneous, intraperitoneal, nasal, hypoglossal, intramuscular, or rectal application. The tropical application for administrating an eyeball includes intra-vitreous body, eye-circumference, trans-scleral, backward of an eye, sub-tenon or device in an eyeball. The preferred administration depends on the symptom of angiogenesis in an eyeball and the properties of the disease The pharmaceutical composition of the present invention includes more than a pharmaceutically effective amount of peptide. The term "pharmaceutically effective amount of " used herein to mean to be sufficient amount to treat or prevent the eye diseases of the present invention. Generally, in composition for systemic application to treat eye diseases, an effective amount of the composition including the peptide and/or protein of the present invention may be preferably administered within a range of a bout 0.001 to about 100 mg/kg weight.

BRIEF DESCRIPTION OF THE DRAWINGS

These and other features, aspects, and advantages of preferred embodiments of the present invention will be more fully described in the following detailed description, taken accompanying drawings. In the drawings:

FIG. 2).

FIG. 5 is a diagram showing that normal angiogenesis is induced but abnormal angiogenesis is suppressed and the vascular leakage is decreased by the polypeptide comprising a RGD sequence(SEQ ID NO: 4—FIG. 5A) and the polypeptide comprising a RGD sequence(SEQ ID NO: 5—FIG. 5B) and the polypeptide comprising a RGD sequence(SEQ ID NO: 6—FIG. 5C) when the polypeptides are administered intraperitoneally in an animal model where mouse retinal angiogenesis is induced by lowering the high oxygen pressure to a normal oxygen partial pressure after the high-pressure oxygen treatment (75%).

BEST MODES FOR CARRYING OUT THE INVENTION

Hereinafter, non-limiting preferred embodiments of the present invention will be described in detail with reference to the accompanying drawings.

EXAMPLE 1

Effects of RGD Sequence-Comprising Polypeptide (SEQ ID NO: 3) in Mouse Model for Inducing Retinal Angiogenesis Using Oxygen Partial Pressure The artificial ocular angiogenesis by oxygen partial pressure difference exhibited the same pattern as in human retinopathy of prematurity and diabetic retinopathy. This experiment was carried out using a principle that abnormal angiogenesis is spontaneously induced when a mouse is subject to a high oxygen environment (75%) at an early stage of its birth, and then returned to a normal oxygen partial pressure (20%) (Higgins R D. et al., Curr. Eye Res. 18:20-27 (1999); Bhart N. et al., Pediatric Res. 46:184-188 (1999); Gebarowska D. et al., Am. J. Pathol. 160:307-313 (2002)). For this purpose, a mouse was kept for 5 days under a high oxygen environment with a constant 75% oxygen partial pressure 7 days after the mouse was born in an apparatus that can adjust an oxygen partial pressure, and then kept under a 20% oxygen pressure which is a normal oxygen partial pressure. At this time, the peptide (SEQ ID NO: 3) comprising a RGD sequence was administered intraperitoneally once every five days to observe whether or not the angiogenesis was induced in the mouse eye. In order to observe the blood vessels, 50 mg of FITC-dextran having a molecular weight of $2 \times 10^6$ was dissolved in 1 ml of saline, and the resultant solution was injected through the left ventricle. The mouse eyeball was extracted immediately after the injection. The extracted eyeball was washed with saline, fixed with 1% paraformaldehyde for 4 to 24 hours, and then a lens was removed from the eyeball. Then, the resultant mouse retina was evenly spread over a glass slide, and the glass slide was sealed with glycerine-gelatin, and then observed using a fluorescence microscope.

Figure 1:
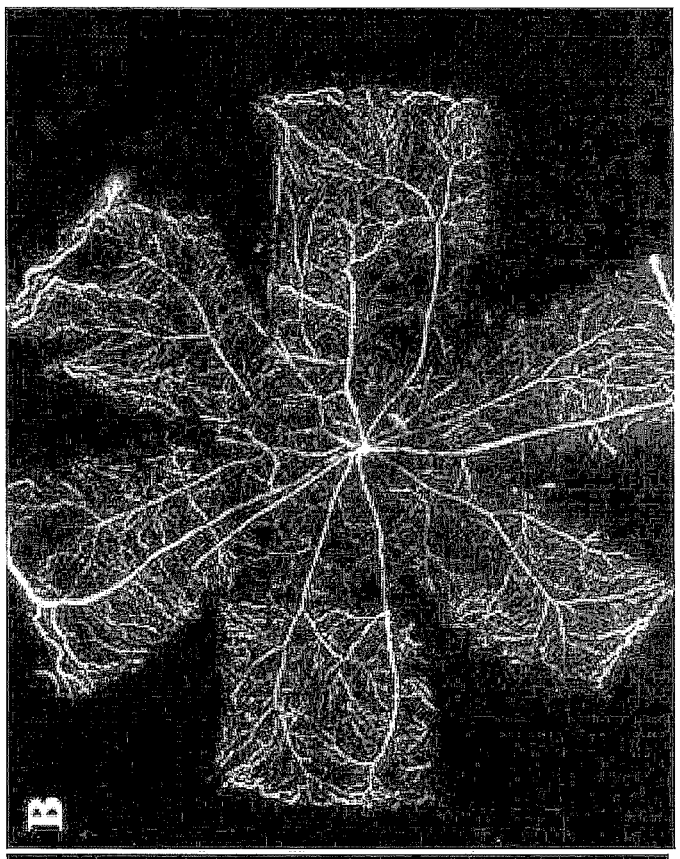
FIG. 1 is a diagram using a fluorescent FITC-dextran, showing comparison of a retina (FIG. 1A) whose mouse does not exhibit a normal angiogenesis and a retina (FIG. 1B) whose mouse normally grows in a normal oxygen partial pressure when the mouse retina is exposed to a high oxygen pressure in an animal model where mouse retinal angiogenesis is induced by lowering the high oxygen pressure to a normal oxygen partial pressure after the high-pressure oxygen treatment (75%).
Figure 1:
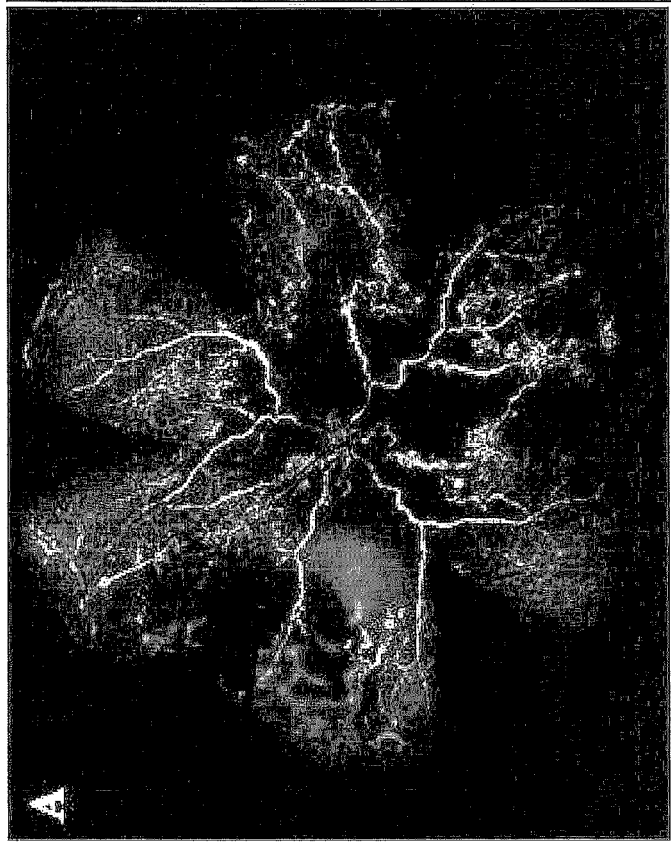
Figure 2:
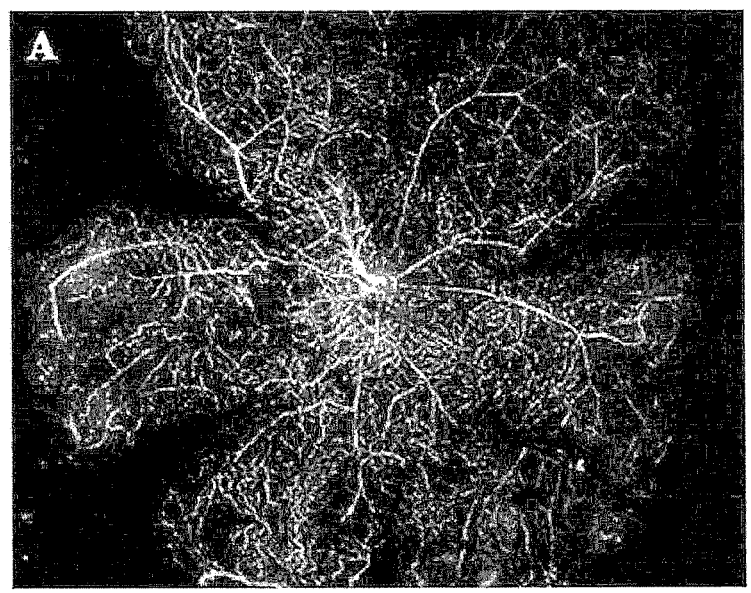
FIG. 2 is a microscopic diagram showing that the new normal vessels normally are formed, and vascular leakage is decreased by the polypeptide comprising a RGD sequence (SEQ ID NO 3—FIG. 2) when the polypeptide is administered intraperitoneally in an animal model where mouse retinal angiogenesis is induced by lowering the high oxygen pressure to a normal oxygen partial pressure after the high-pressure oxygen treatment (75%).

It was observed that the blood vessels was uniformly distributed over the entire retina of the mouse that grown in a normal oxygen partial pressure (B of FIG. 1), and the most angiogenesis was abnormal and the ischemia was developed in the mouse that was treated with the high-pressure oxygen and then the saline (A of FIG. 1). However, it was revealed that the abnormal angiogenesis was not observed as well as the normal blood vessels were observed in the mouse treated with 100 ug/kg/day of the polypeptide(SEQ ID NO: 3) comprising a RGD sequence (A of FIG. 2).

Figure 3:
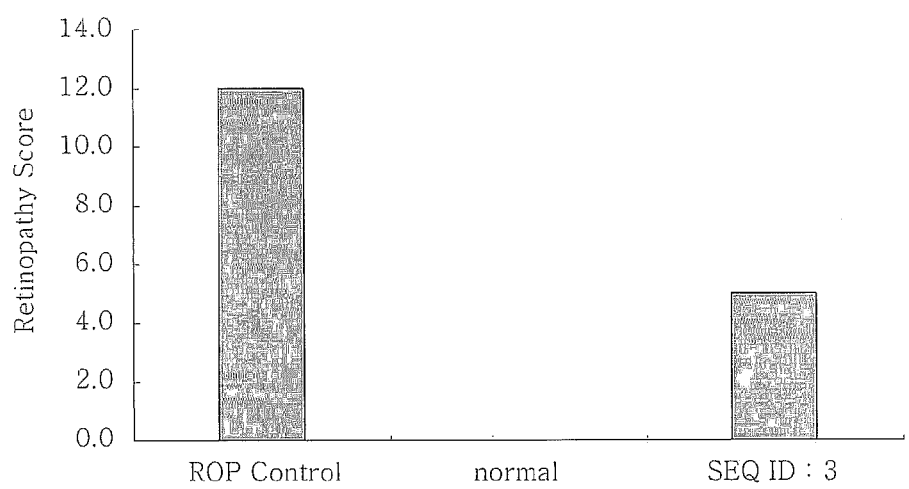
FIG. 3 is a comparison graph showing that a retinopathy score between the experimental groups is digitalized by employing the method accessing the retinopathy score disclosed in Higgins R. D. et al.,(Curr. Eye Res. 18:20-27, 1999), compared to a retina (FIG. 1-A) exposed to a high oxygen pressure (75%) whose mouse does not exhibit a normal angiogenesis and a retina (FIG. 1-B) whose mouse normally grows in a normal oxygen partial pressure and a retina(FIG. 2-A) of mouse which is administered intraperitoneally with the polypeptide comprising a RGD sequence (SEQ ID NO: 3).
Figure 4:
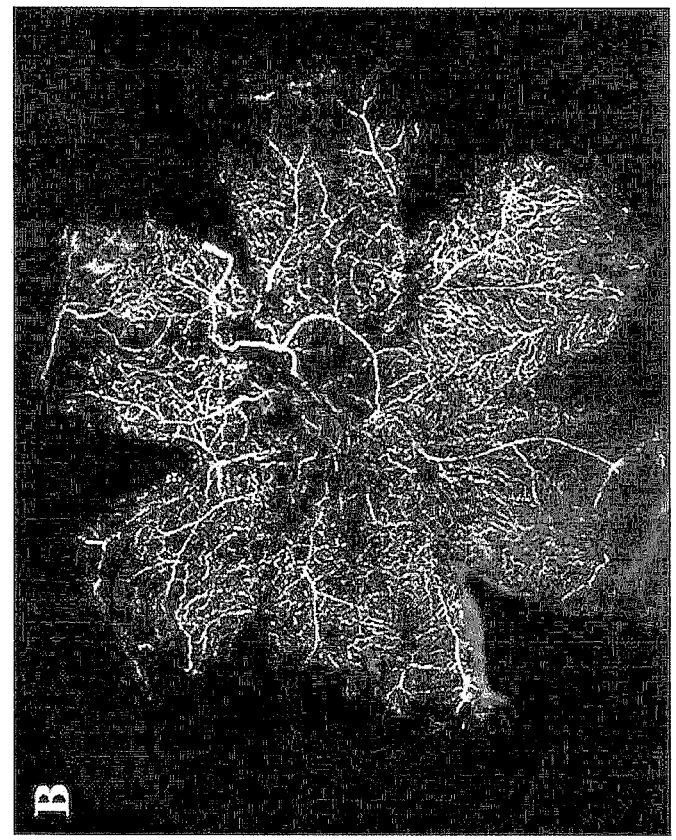
FIG. 4 is a diagram showing that normal angiogenesis is induced but abnormal angiogenesis is suppressed by the polypeptide comprising a RGD sequence (SEQ ID NOs: 1 and 2—FIGS. 4. A, B) when the polypeptide comprising a RGD sequence is administered intraperitoneally in an animal model where mouse retinal angiogenesis is induced by lowering the high oxygen pressure to a normal oxygen partial pressure after the high-pressure oxygen treatment (75%).This figure reveal that the polypeptides comprising a RGD sequence(SEQ ID NOs: 1 and 2) have the same advantageous effect as the polypeptide comprising a RGD sequence (SEQ ID NO: 3.
Figure 4:
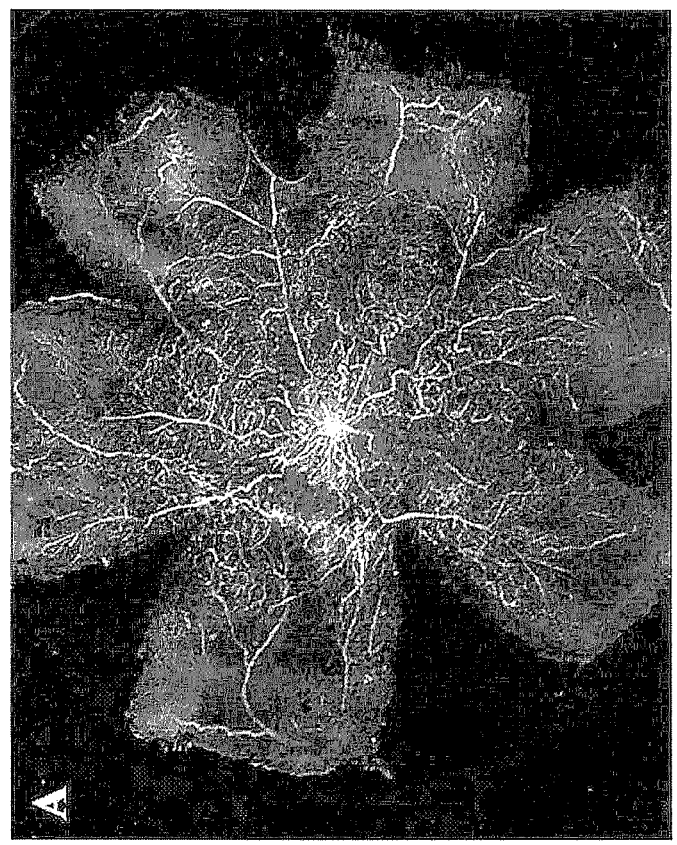

The degree on abnormal vessel, avascular lesion and vascular leakage caused by the retinopathy was digitalized and the retinopathy score was compared. (Higgins R. D. et al., Curr. Eye Res. 18:20-27, 1999) The result showed that mouse normally grows in a normal oxygen partial pressure was 0 and the abnormal vessel was not observed, but mouse led to retinopathy by exposing to a high oxygen pressure was 12 and the abnormal vessel was significantly observed. While mouse which was administered with the polypeptide comprising a RGD sequence was 5 and about 60% of the abnormal vessel caused by a high oxygen pressure was normalized (FIG. 3). This is a very interesting result in that the polypeptide comprising a RGD sequence functions to help growth of normal blood vessels. Accordingly, the polypeptide (SEQ ID NO: 3) comprising a RGD sequence may be used as a therapeutic agent for treating ocular diseases avascular and abnormal angiogenesis such as diabetic retinopathy and age-related macular degeneration.

EXAMPLE 2

Effects of RGD Sequence-Comprising Polypeptide (SEQ ID NOs: 1, 2 and 3) in Mouse Model for Inducing Retinal Angiogenesis Using Oxygen Partial Pressure In Example 2, an effect of the polypeptide (SEQ ID NOs: 1, 2 and 3) comprising a RGD sequence was confirmed in a mouse model for inducing an artificial retinal angiogenesis using oxygen partial pressure, as described in Example 1. It was confirmed that the blood vessels are uniformly distributed over the entire retina in the mouse that grows in a normal oxygen partial pressure as described in Example 1 (B of FIG. 1), and the most angiogenesis was abnormal and the ischemia was developed in the mouse that was treated with the high-pressure oxygen and then the saline (A of FIG. 1). It was revealed that the abnormal angiogenesis was decreased and the normal blood vessels were observed in the mouse treated with all polypeptides (SEQ ID NOs: 1, 2 and 3) comprising a RGD sequence (A, B and C of FIG. 3). Especially, the polypeptide (SEQ ID NO: 3) comprising a RGD sequence decreased the abnormal angiogenesis more than the polypeptide (SEQ ID NOs: 1 and 2) comprising a RGD sequence and the form of the vessel was like normal vessel. The result means that the polypeptide (SEQ ID NO: 3) comprising a RGD sequence functions to help growth of normal blood vessels, as described in Example 1. Accordingly, this result means that not only RGD sequence but also the longer peptide sequence comprising a RGD sequence is necessary for the growth of normal blood vessels.

EXAMPLE 3

Effects of RGD Sequence-Comprising Polypeptide (SEQ ID NOs: 3, 4, 5 and 6) in Mouse Model for Inducing Retinal Angiogenesis Using Oxygen Partial Pressure In Example 3, an effect of the polypeptide (SEQ ID NO: 3,4,5 and 6) comprising a RGD sequence was confirmed in a mouse model for inducing an artificial retinal angiogenesis using oxygen partial pressure, as described in Example 1. It was confirmed that the blood vessels are uniformly distributed over the entire retina in the mouse that grows in a normal oxygen partial pressure as described in Example 1 (B of FIG. 1), and the most angiogenesis was abnormal and the ischemia was developed in the mouse that was treated with the high-pressure oxygen and then the saline (A of FIG. 1). It was revealed that the abnormal angiogenesis, avascular lesion and vascular leakage were decreased and the normal blood vessels were observed in the retina treated with all polypeptides (SEQ ID NOs: 3, 4, 5 and 6) comprising a RGD sequence (A, of FIGS. 2, A, B and C of FIG. 6). The result means that the polypeptide(SEQ ID NOs: 4, 5, and 6) comprising a RGD sequence functions to help growth of normal blood vessels, as described in Example 1. And in addition to a TP508 (SEQ ID NO: 3), a Thrombin, the larger protein(SEQ ID NO: 4) comprising the TP508 comprising the TP508, a protein(SEQ ID NO: 5) comprising the TP508 but the size is smaller than the thrombin and a smaller peptide(SEQ ID NO: 6) than the TP508 had a similar effect as the TP508. Accordingly, all peptides comprising a RGD sequence including TP508 may be used as a therapeutic agent for treating ocular diseases avascular and abnormal angiogenesis such as diabetic retinopathy and age-related macular degeneration, irrespective of the size of the peptide.

The peptides and their sequences of the present invention are as follows, the peptide of SEQ ID NO: 4 was purchased from Sigma company (U.S.A.) and the peptides of SEQ ID NOs: 1 and 2 were purchased from BACHEM (Germany) and the peptides of SEQ ID NOs: 3, 5 and 6 were prepared by chemical synthesis (Peptron., Daejeon, Korea).

SEQ ID NO: 1:
Cyclo(-Arg-Gly-Asp-D-Phe-Val)

SEQ ID NO: 2:
H-Gly-Phe-Gly-Arg-Gly-Asp-Ser-Pro-Cys-Ala-OH

SEQ ID NO: 3:
Ala Gly Tyr Lys Pro Asp Glu Gly Lys Arg Gly Asp
Gly Asp Ala Cys Glu Gly Asp Ser Gly Gly Pro Phe
Val

SEQ ID NO: 4:
Met Ala His Val Arg Gly Leu Gln Leu Pro Gly Cys
Leu Ala Leu Ala Ala Leu Cys Ser Leu Val His Ser
Gln His Val Phe Leu Ala Pro Gln Gln Ala Arg Ser
Leu Leu Gln Arg Val Arg Arg Ala Asn Thr Phe Leu
Glu Glu Val Arg Lys Gly Asn Leu Glu Arg Glu Cys
Val Glu Glu Thr Cys Ser Tyr Glu Glu Ala Phe Glu
Ala Leu Glu Ser Ser Thr Ala Thr Asp Val Phe Trp
Ala Lys Tyr Thr Ala Cys Glu Thr Ala Arg Thr Pro
Arg Asp Lys Leu Ala Ala Cys Leu Glu Gly Asn Cys
Ala Glu Gly Leu Gly Thr Asn Tyr Arg Gly His Val
Asn Ile Thr Arg Ser Gly Ile Glu Cys Gln Leu Trp
Arg Ser Arg Tyr Pro His Lys Pro Glu Ile Asn Ser
Thr Thr His Pro Gly Ala Asp Leu Gln Glu Asn Phe
Cys Arg Asn Pro Asp Ser Ser Thr Thr Gly Pro Trp
Cys Tyr Thr Thr Asp Pro Thr Val Arg Arg Gln Glu
Cys Ser Ile Pro Val Cys Gly Gln Asp Gln Val Thr
Val Ala Met Thr Pro Ser Arg Glu Gly Ser Ser Val
Asn Leu Ser Pro Pro Leu Glu Gln Cys Val Pro Asp
Arg Gly Gln Gln Tyr Gln Gly Arg Leu Ala Val Thr
Thr His Gly Leu Pro Cys Leu Ala Trp Ala Ser Ala
Gln Ala Lys Ala Leu Ser Lys His Gln Asp Phe Asn
Ser Ala Val Gln Leu Val Gln Asn Phe Cys Arg Asn
Pro Asp Gly Asp Glu Glu Gly Val Trp Cys Tyr Val
Ala Gly Lys Pro Gly Asp Phe Gly Tyr Cys Asp Leu
Asn Tyr Cys Glu Glu Ala Val Glu Glu Glu Thr Gly
Asp Gly Leu Asp Glu Asp Ser Asp Arg Ala Ile Glu
Gly Arg Thr Ala Thr Ser Glu Gly Gly Thr Phe Phe
Asn Pro Arg Thr Phe Gly Ser Gly Glu Ala Asp Cys
Gly Leu Arg Pro Leu Phe Glu Lys Lys Ser Leu Glu
Asp Lys Thr Glu Arg Glu Leu Leu Glu Ser Tyr Ile
Asp Gly Arg Ile Val Glu Gly Ser Asp Ala Glu Ile
Gly Met Ser Pro Trp Gln Val Met Ile Phe Gly Met
Ser Pro Trp Gln Val Met Cys Gly Ala Ser Leu Ile
Ser Asp Arg Trp Val Leu Thr Ala Ala His Cys Leu
Leu Tyr Pro Pro Trp Asp Lys Asn Phe Thr Glu Asn
Asp Leu Leu Val Arg Ile Gly Lys His Ser Arg Thr
Arg Tyr Glu Arg Asn Ile Glu Ser Ile Ser Met Leu

-continued

Glu Lys Ile Tyr Ile His Pro Arg Tyr Asn Trp Arg
Glu Asn Leu Asp Arg Asp Ile Ala Leu Met Lys Leu
Lys Lys Pro Val Ala Phe Ser Asp Tyr Ile His Pro
Val Cys Leu Pro Asp Arg Glu Thr Ala Ala Ser Leu
Leu Gln Ala Gly Tyr Lys Gly Arg Val Thr Ala Asn
Val Gly Lys Gly Gln Pro Trp Thr Ala Asn Val Gly
Lys Gly Gln Pro Ser Val Leu Gln Val Val Asn Leu
Pro Ile Val Glu Arg Pro Val Cys Lys Asp Ser Thr
Arg Ile Arg Ile Thr Asp Asn Met Phe Cys Ala Gly
Tyr Lys Pro Asp Glu Gly Lys Arg Gly Asp Gly Asp
Ala Cys Glu Gly Asp Ser Gly Gly Pro Phe Val Met

Lys Ser Pro Phe Asn Asn Arg Trp Tyr Gln Met Gly
Ile Val Ser Trp Gly Glu Gly Cys Asp Arg Asp Gly
Lys Tyr Gly Phe Tyr Thr His Val Phe Arg Leu Lys
Lys Trp Ile Gln Lys Val Ile Asp Gln Phe Gly Glu

SEQ ID NO: 5:
Arg Ile Arg Ile Thr Asp Asn Met Phe Cys Ala Gly
Tyr Lys Pro Asp Glu Gly Lys Arg Gly Asp Gly Asp
Ala Cys Glu Gly Asp Ser Gly Gly Pro Phe Val Met
Lys Ser Pro Phe Asn Asn

SEQ ID NO: 6:
Thrombin derivative-2 (Synthesized)
Asp Glu Gly Lys Arg Gly Asp Gly Asp Ala Cys Glu
Gly Asp Ser

---

What is claimed is:

1. A method for treating retinopathy, comprising administering to a subject a pharmaceutical composition containing a thrombin-derived peptide comprising the amino acid sequence set forth in SEQ ID NO:6 as an effective component, wherein the treatment for the retinopathy is indicative of decreasing abnormal angiogenesis, decreasing vascular leakage or assisting stabilization of blood vessels, and wherein the retinopathy is selected from the group consisting of diabetic retinopathy, retinopathy of prematurity, and wet age-related macular degeneration.

2. The method according to claim 1, wherein the thrombin-derived peptide comprises the amino acid sequence set forth in SEQ ID NO:3.

3. The method according to claim 1, wherein the thrombin-derived peptide comprises the amino acid sequence set forth in SEQ ID NO:5.

4. The method according to claim 1, wherein the thrombin-derived peptide comprises the amino acid sequence set forth in SEQ ID NO:4.

* * * * *